US005575649A

United States Patent [19]
Lee

[11] Patent Number: 5,575,649
[45] Date of Patent: Nov. 19, 1996

[54] DENTAL RESTORATION HOLDER SYSTEM

[76] Inventor: Robert L. Lee, 22937 Grand Terrace Rd., Grand Terrace, Calif. 92324

[21] Appl. No.: 220,115

[22] Filed: Mar. 30, 1994

Related U.S. Application Data

[63] Continuation-in-part of Ser. No. 836,065, Feb. 12, 1992, Pat. No. 5,320,533, and a continuation-in-part of Ser. No. 196,420, Feb. 15, 1994.

[51] Int. Cl.⁶ .................................. A61C 3/00; A61C 5/08
[52] U.S. Cl. ............................................. 433/141; 433/218
[58] Field of Search .................................. 433/3, 141, 163, 433/215, 218, 219, 229; 40/641, 359; 294/1.1, 1.2, 25, 902; 206/0.8, 0.84

[56] References Cited

U.S. PATENT DOCUMENTS

| | | | |
|---|---|---|---|
| 638,785 | 12/1899 | Whittlesey | 206/0.84 |
| 730,184 | 6/1903 | Witter | 433/141 X |
| 1,106,815 | 8/1914 | Hopkins . | |
| 1,202,698 | 10/1916 | Ford . | |
| 1,515,638 | 11/1924 | Wason | 206/0.84 |
| 1,622,616 | 3/1927 | Temple | 433/215 X |
| 1,647,922 | 11/1927 | Linder | 206/0.84 |
| 1,809,423 | 6/1931 | Peck . | |
| 1,990,381 | 2/1935 | Ivory . | |
| 2,257,669 | 9/1941 | Beckmann | 433/163 |
| 2,397,740 | 4/1946 | Johnshoy | 206/0.84 |
| 2,567,794 | 9/1951 | Winett . | |
| 2,954,866 | 10/1960 | McDermut | 206/0.84 |
| 3,080,963 | 3/1963 | Rothgart | 206/0.84 |
| 3,285,409 | 11/1966 | Loran . | |
| 3,628,249 | 12/1971 | Wurl . | |
| 3,748,741 | 7/1973 | Yerkees, Jr. . | |
| 3,974,567 | 8/1976 | Ridgeway . | |
| 4,073,530 | 2/1978 | Seidler . | |
| 4,185,384 | 1/1980 | Lustig et al. . | |
| 4,219,619 | 8/1980 | Zarow . | |
| 4,265,618 | 5/1981 | Herskovitz et al. . | |
| 4,293,074 | 10/1981 | Dunsky . | |
| 4,382,784 | 5/1983 | Freller . | |
| 4,486,177 | 12/1984 | Lekawa . | |
| 4,664,628 | 5/1987 | Totaro . | |
| 4,681,358 | 7/1987 | Smith | 294/1.1 X |
| 4,725,233 | 2/1988 | Planert . | |
| 4,773,857 | 9/1988 | Herrin . | |
| 4,834,654 | 5/1989 | Nussbaum . | |
| 4,919,615 | 4/1990 | Croll . | |
| 4,953,902 | 4/1990 | Brown . | |
| 4,975,053 | 12/1990 | Hofsess . | |
| 4,993,949 | 2/1991 | Hill . | |
| 5,035,615 | 7/1991 | Din . | |
| 5,040,981 | 8/1991 | Oliva . | |
| 5,098,292 | 3/1992 | Lazarof . | |
| 5,197,877 | 3/1993 | Andrew . | |
| 5,197,878 | 3/1993 | Lukase et al. . | |

FOREIGN PATENT DOCUMENTS 4027955  12/1991  Germany .

Primary Examiner—Nicholas D. Lucchesi
Attorney, Agent, or Firm—Knobbe, Martens, Olson & Bear

[57] ABSTRACT

A small, thin, flat, stiff tab is glued with a hot melt adhesive to the exterior surface of a dental restoration. The tab can then be gripped between a thumb and forefinger while placing the restoration on a tooth to which it is to be laminated. After the restoration is placed on the tooth with permanent bonding material between the restoration and the tooth, the tab is used as a vibrating transmitter to the restoration. The tab is vibrated by positioning a flat-sided dental shaft against an edge of a hole in the tab and rotating the shaft with a dental handpiece. A group of tabs are conveniently supported in slots formed in the upper surface of a support. The slots are dimensioned in relation to the tabs in a manner such that one end of a tab is in a slot while the finger gripping area of the tab extends upwardly, away from the support for convenient gripping by a person's fingers.

19 Claims, 3 Drawing Sheets

DENTAL RESTORATION HOLDER SYSTEM

CROSS-REFERENCE TO RELATED APPLICATION

This application is a continuation-in-part of U.S. patent application Ser. No. 07/836,065 filed Feb. 12, 1992, now U.S. Pat. No. 5,320,533 and U.S. patent application Ser. No. 08/196,420, filed Feb. 15, 1994, now pending.

FIELD OF THE INVENTION

The present invention relates generally to dental techniques and equipment, and more specifically to a system for facilitating the positioning of tooth veneers or other dental restorations on patient's teeth and in the handling of such restorations in the laboratory.

BACKGROUND OF THE INVENTION

For a variety of reasons, the enamel surfaces of teeth sometimes become permanently stained, decayed or damaged. A technique has been developed to repair or improve the appearance and function of such teeth.

In a procedure referred to as cosmetic bonding, a thin veneer of ceramic or plastic having a shape and curvature matching the outline, shape and surface curvature of a tooth to be refaced is bonded to the facial or labial surface of the tooth, after the tooth has been specially prepared. The veneer has a desired surface coloration and gloss to match adjacent teeth. The veneer is sufficiently opaque to mask a stained surface of the underlying tooth. By this procedure, teeth may be restored to a more pleasing and functional appearance.

Cosmetic bonding includes a sequence of steps requiring exercise of a substantial degree of artistic craftsmanship. The dentist must prepare each tooth to receive a veneer and make accurate impressions of the prepared teeth. Teeth impressions are made by forming a dental impression material over the teeth and allowing the material to harden. Impressions are then used by a dental ceramist or a dentist to make a veneer. In one procedure the impressions are used to make molds in which the required ceramic veneers are eventually fabricated. Each veneer is individually fabricated and must have the desired precise dimensions, coloration, luster, and opacity.

The number of individually demanding steps required to fabricate each tooth veneer results in a substantial investment in time. Thus, the replacement value of each custom-made veneer is significant. Accordingly, considerable care must be exercised in handling a veneer to avoid damage to it. The veneer is relatively fragile until it has been bonded or laminated to and supported by the tooth for which it was custom-fabricated.

After a number of preparation steps, the veneer is temporarily placed on the appropriate tooth. The purpose of the temporary placement is to check size, opacity and coloration of the veneer. After this preliminary testing, the veneer is removed, and both the veneer and tooth thoroughly cleaned of the temporary adhesive and dried. The veneer or other restoration is then permanently bonded to the supporting tooth. Typically this is done with a light sensitive bonding agent. The inner surface of the restoration is coated with such bonding agent, and the restoration placed in position on the tooth. All of these procedures are usually performed by the dentist holding the substantially small, fragile restoration between his or her thumb and forefinger. Needless to say, many of these small restorations are inadvertently dropped or damaged during the fitting, adjustment and placement phase.

Another difficulty encountered in positioning and permanently bonding a restoration to a tooth concerns the permanent bonding agent employed. One type that is frequently utilized is a composite resin that is fairly viscous or stiff. The material should, of course, be spread between all of the mating surfaces of the restoration and the base tooth. It is also desirable that any excess bonding agent be squeezed out from between the restoration and the tooth. In one current attempt at accomplishing this, the dentist will press a finger on the restoration and roll the finger from side to side, while balancing the force with a finger on the backside of the tooth. This is not a very effective method. Dental crowns are sometimes seated using a vibrating pad clamped between the crown and the mating tooth and the opposing jaw. This method cannot be used with a veneer since there is no mating biting surface.

After the bonding agent spreading step is completed, the bonding agent is cured. Typically this is accomplished by irradiating the outer surface of the restoration with a small intense light source. Light transmitted through the restoration produces a photo-chemical reaction in the bonding agent, causing it to harden.

During the light exposure process, which takes between 20 and 60 seconds, the dentist must hold the restoration in a precisely aligned position with respect to the tooth. If the restoration is displaced from its aligned position during the bonding process, the restoration may have to be ground off the tooth, and a replacement restoration fabricated.

Because of the difficulty of handling and positioning the restoration, a variety of tools and techniques have been developed. These prior systems have various disadvantages such as complexity, difficulty in using or ineffectiveness. Thus, it is believed that many restorations are positioned only with fingers. Accordingly, a need exists for an improved, simplified tool and technique for handling veneers and other restorations. There is also a need for improving the means for spreading the bonding agent that joins the restoration to the underlying tooth.

SUMMARY OF THE INVENTION

Briefly stated, a small, relatively flat, thin, stiff element forms a tab-like holder for manipulating and positioning a tooth restoration such as a veneer, crown or inlay. One edge of the planar element is attached to the outer surface of the restoration with an adhesive which provides a firm attachment that is sufficiently strong when solidified to hold the element in an edge-wise position with respect to the restoration. That is, the element extends generally perpendicular to the restoration outer surface to form a tab attached to the restoration. This enables the restoration to be positioned and manipulated by simply gripping the tab between the thumb and a finger of one hand. With that arrangement, the thumb and finger are engaging or are close to the restoration, which greatly facilitates control and positioning of the restoration on the patient's tooth.

In the preferred form of the invention, the adhesive employed is solid at room temperature, although slightly resilient, but becomes flowable when heated. A preferred example of that is a hot-melt adhesive, which can be conveniently heated by and dispensed from a glue gun. Preferably, a quantity of heated glue is applied to the restoration and to an edge of the tab, and the two are then joined in a desired position. In use with a tooth veneer, the planar tab is desirably oriented either vertically or horizontally with respect to the long axis of the veneer, as it would be placed on the tooth.

The tab may be made of various materials, but is preferably made of a plastic, such as nylon. Further, the tab in one arrangement has a pair of spaced edge points on the edge to be attached to the restoration. This creates a recessed area in the edge portion between these points. An advantage of this arrangement is that the two points form an attachment base with flat or curved restoration surfaces. Also, the adhesive can surround the two points and fit within the recess as well. Also, there may be provided a small hole in each of the points that fills with adhesive. This enables a small quantity of adhesive around that edge of the tab to bond the tab to the restoration in the desired position. Preferably, a hole is also formed in the finger-gripping area of the tab to facilitate the gripping action. This same hole may be conveniently used for attaching a string or floss for purposes of retrieving the restoration and the tab from the patient's mouth in the event the tab is dropped.

The hole in the finger gripping area of the tab also serves an additional function in connection with proper bonding of the restoration to the tooth. After the permanent bonding agent has been applied to the restoration and the restoration has been positioned on the tooth, utilizing the tab, and before curing the bonding agent, a vibrating tool may be inserted into the opening in the finger gripping area of the tab and pressed against the edge of the hole closest to the restoration. Alternatively, the tool can be placed against the edge of the tab remote from the edge secured to the restoration. This causes vibration to be transmitted from the tab to the restoration and thus to the bonding agent. This action causes the bonding agent between the restoration and the tooth to be evenly distributed and causes excess bonding agent to be extruded out around the edges of the restoration. The vibrating tool may be in the form of a shaft having a flat-sided cross-section, with the shaft being rotated by a dental hand piece, and the side of the tool being placed against the tab edge.

After the vibration step, a curing light is applied to the restoration to cure the bonding agent between the restoration and the tooth. When that operation is complete, water sprayed onto the restoration will cause the adhesive between the restoration and the tab to be released from the restoration so that the tab together with that adhesive may be removed from the restoration and discarded.

As another feature of the invention, there is provided a support for conveniently positioning a group of tabs. The lower end of each tab fits within a slot in the upper wall of the support, with the finger gripping area on each tab extending upwardly. With that arrangement, the dentist may conveniently grip the tab with the thumb and forefinger from above in exactly the orientation that is desired when the tab is to be attached to the dental restoration and the restoration is to be positioned on the patient's tooth or on a tooth model in the laboratory. The support is relatively short so that the middle finger or ring finger of the gripping hand may engage a surface on which the support is positioned, so as to stabilize the hand when a tab is being gripped with the thumb and forefinger.

DETAILED DESCRIPTION OF THE INVENTION

Figure 1:
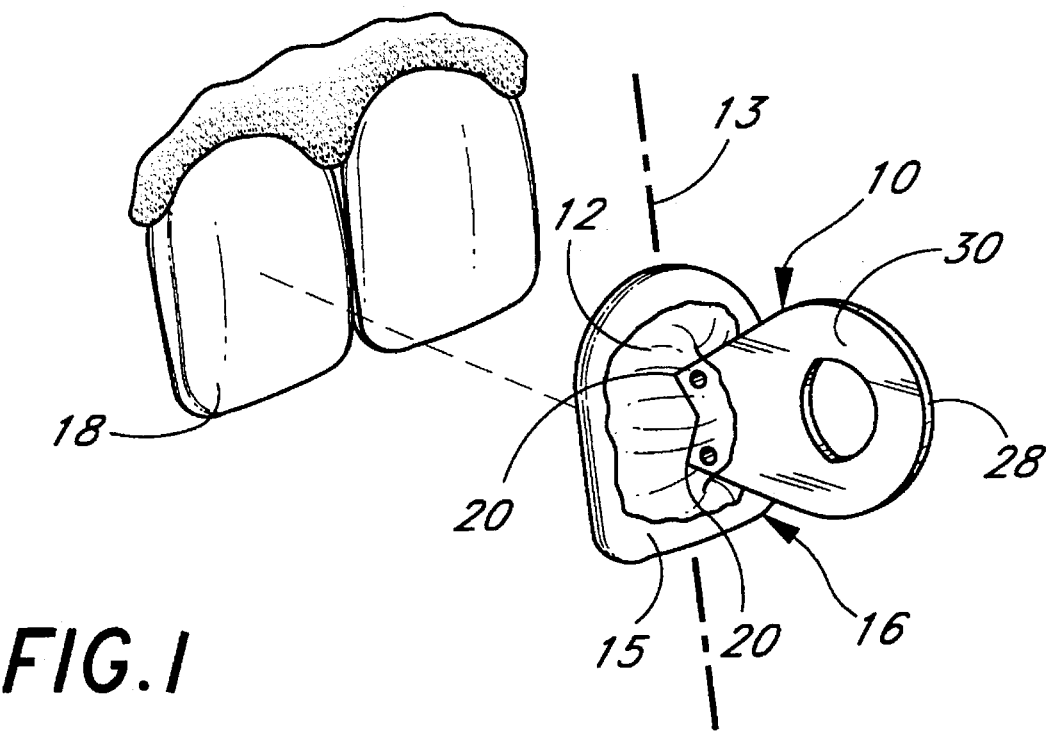
FIG. 1 is an enlarged perspective view illustrating the placement tab of the invention joined to the outer surface of a tooth veneer.
Figure 2:
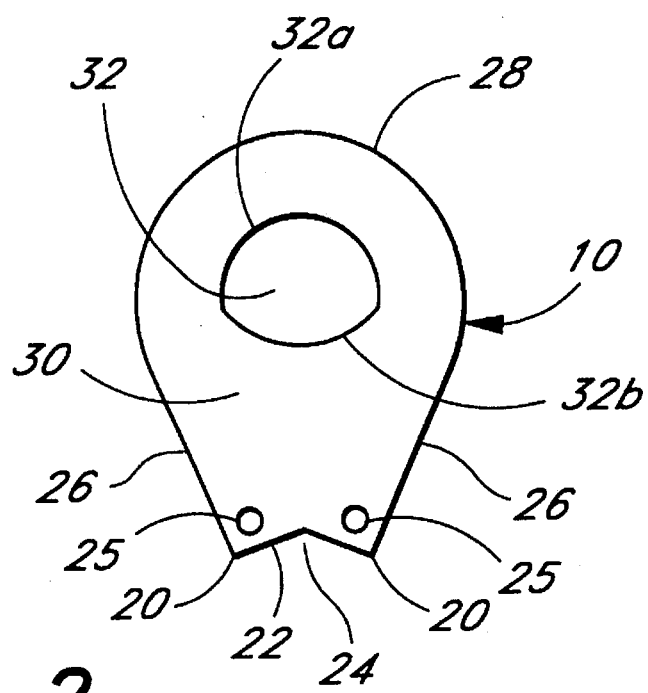
FIG. 2 is a plan view of the pad of FIG. 1.

FIG. 1 illustrates a holder placement tab 10 attached by adhesive 12 to the outer surface 15 of a dental restoration in the form of a ceramic veneer 16. The tab is expected to be most useful for positioning a veneer as shown but it can of course be used for crowns and inlays or other dental restorations, either in the mouth or on a laboratory model. The tab 10 is in the form of a thin, relatively flat, stiff element which is preferably made of plastic or nylon. Of course, the tab can be made of other materials such as cardboard, wood, or metal. Referring to the plan view of FIG. 2, it may be seen that the tab has a lower or leading edge 22 to engage the veneer. This edge 22 is defined by a pair of spaced end points 20 which are joined by a shallow V-shaped portion that defines a shallow recess 24. In a preferred form of the invention, the angle of the V-shaped recess is about 138°. A small hole 25 is formed near each of the points 20 to receive adhesive used to connect the tab to the veneer.

The tab 10 further has side edges 26 which diverge slightly from the points 20 to a maximum width and merge into a semi-circular upper edge 28. The portion of the tab which is not covered by the adhesive 12 in FIG. 1 forms a finger-gripping area 30. More specifically, there is an area gripped by a thumb and one finger of a person's hand, usually the forefinger, as seen in FIG. 3.

To facilitate gripping the tab, there is formed an opening 32 in the finger gripping area having upper end lower curved edges 32a and 32b which give the hole somewhat of a lemon shape.

An important feature of the invention is that the lower end of the tab has to mate with veneers or other dental restorations having various curvatures. Regardless of the curvature, the two points 20 will engage the veneer surface, thus providing a good base for connection to the veneer. Also, the recess 24 forms a pocket for receiving adhesive and helps adequately attach the tab to the veneer. The points 20 are spaced to accommodate most veneers. The preferred spacing is about 4 mm. Such dimension will allow the tab points 20 to make contact with very small veneers. Of course other dimensions may be employed.

Figure 3:
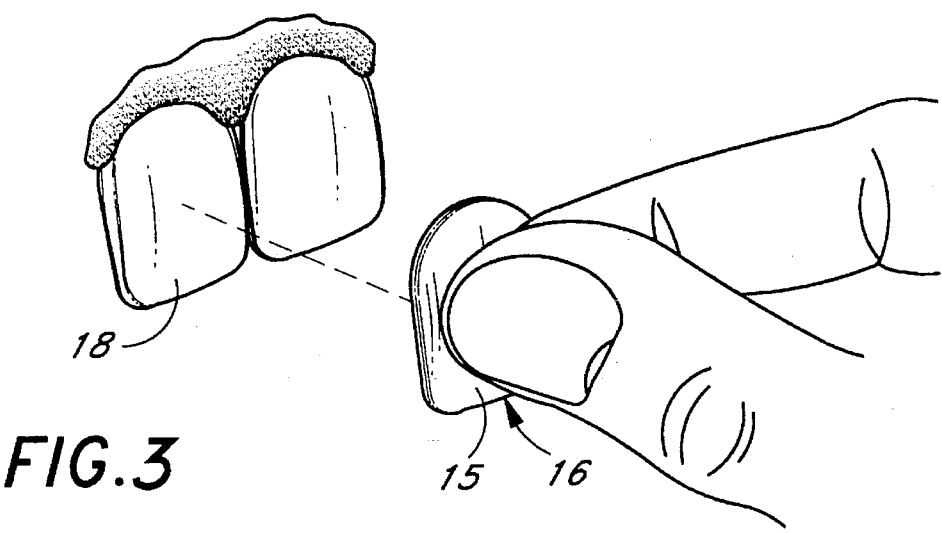
FIG. 3 shows the tab transmitting vibration to the veneer.

One of the other features of the invention is that the tab is to be gripped immediately adjacent the veneer so as to provide good control in the positioning of the veneer on a tooth 18, as shown in FIG. 3. For that reason and for ease of handling, it is desirable that the tab be no bigger than necessary to enable it to be conveniently gripped between the thumb and forefinger of a person's hand. This may be referred to as gripped by "the fingers". The illustration is from the perspective of a viewer in front of the patient. The view from the dentist's perspective would probably be inverted since the dentist is usually positioned behind and above the patient.

In a preferred embodiment of the tab, the width of the tab at its widest, where the side edges 26 merge with the upper edge 28, is a little under 10, and the distance from the points 20 and a tangent through the center of the upper edge 28 of the tab is only about 13 mm. Thus the tab is about the size of a penny or smaller, preferably only about the size of a small fingernail. These dimensions can be somewhat larger, but the tab flat side should be no greater than one inch in any direction, in that it then becomes cumbersome to use. The tab planar dimensions are much greater than its thickness, preferably only about 0.030 inches (0.8 mm) thick.

It is desirable that the hole 32 in the tab be as large as possible, consistent with strength and the overall small size of the tab, so that a person's forefinger and thumb can protrude slightly into the opening when the tab is being gripped. The maximum width of the hole in the preferred form of the invention is about 5 mm and the maximum height is about 3 mm.

The adhesive 12 securing the tab to the veneer is preferably a hot-melt glue which is available in rod form and is electrically heated by a conventional glue gun. The glue is a thermoplastic material which is solid at room temperature but will soften and become molten as it is heated. The material is quite sticky when heated and will remain attached to the placement tab and the veneer as it solidifies. When solidified, the glue provides a strong attachment, but at the same time, it is slightly resilient so that it is comfortable to grip and provides a good "feel" for positioning purposes.

An adhesive which is currently preferred is marketed by H.B. Fuller Company, located at 1200 Walters Boulevard, Vadnais Heights, Minn. 55110. It is identified by that company as 9081-X. The exact composition of the adhesive is proprietary to that company, but it is understood that the primary component of the adhesive is ethylene vinyl acetate. Other adhesives with suitable characteristics are also probably available. Any suitable commercial glue gun is satisfactory. The adhesive may also be heated by the flame of a bunsen burner, alcohol torch or other means; however, an electrically heated adhesive dispenser is believed to be most convenient.

In utilizing the positioning tab of the invention, the restoration to be attached is initially typically mounted on a tooth model. A quantity of heated adhesive may be smeared onto the outer surface of the veneer. A quantity is also positioned on the lower edge of the placement tab. The lower edge of the tab is then immediately positioned against the veneer and the tab held there as the adhesive solidifies. This only takes a few seconds. Preferably, the adhesive is spread over the major area of the restoration, perhaps as much as 75% of the surface of a front tooth veneer. This provides a relatively large attachment base to securely attach the tab to the veneer. The adhesive, being on both sides of the tab, readily makes a strong attachment to the tab.

The two points 20 on the lower edge 22 of the tab of course engage the restoration surface and provide a solid base for the attachment. The adhesive 12 flows around those points and into the holes 25, as well as into the recess 24 between the points, as shown in FIG. 1. A major advantage of the point arrangement is that it will conform to various curved exteriors of the restoration. The tab should be positioned so it extends outwardly substantially perpendicular to the surface of the restoration so that it can be conveniently gripped. While the tab can be rotationally oriented in any desired position on the restoration, it has been found that the most convenient arrangement is to position the tab so that its plane is either parallel or perpendicular with respect to a vertical axis 13 of the veneer. With larger veneers, the perpendicular orientation is usually preferable and with smaller veneers, the parallel orientation may be preferred.

After the tab has been solidly attached to the restoration, the restoration can of course be positioned on the tooth or tooth model as many times as desired or as is necessary in the various adjusting, color-matching and bonding steps as needed. The restoration can also be positioned on and off the dental cast in the laboratory. The restoration can also be held by the tab while the restoration is being adjusted with dental tools by either the technician or the dentist.

As noted above, it is desirable to evenly distribute bonding agent between the restoration and the tooth to be laminated. With relatively thick bonding agent it is sometimes difficult to accomplish the distribution and to extrude excess bonding agent from beneath the restoration. One example of a material being used is a composite resin sold under the trademark Herculite. In accordance with another aspect of the invention, a small shaft or bit 34 mounted in a dental handpiece is inserted through the hole 32 in the tab and the side of the shaft is pressed against the hole edge 32b toward the tooth. As seen from FIG. 3, the shaft has a somewhat rectangular cross section, or other noncircular cross section, with the result that when the handpiece is activated, the rotation of the shaft creates a vibrating force which is transmitted into the plane of the tab and directed towards the restoration. This causes the restoration to vibrate and evenly spread the bonding material between the tooth and the restoration, and helps seat the restoration in the proper position. It should be noted that the solidified glue that attaches the tab to the restoration is somewhat resilient, and it distributes the vibrating force applied to the restoration so that the vibrations do not damage the delicate restoration. The vibrating tool could instead be held against the outer tab edge 28. The dentist holds the tab when it is being vibrated, but for convenience the dentist's fingers are not shown in FIG. 3.

The tab can then be once more gripped with the fingers so that the restoration is held stationary and pressed against the tooth 18 until the bonding agent has bonded the restoration to the tooth. The bonding agent that is typically employed for bonding the restoration to the tooth is a light-sensitive agent that will cure when irradiated with a small intense light source. The light source will pass through the thin restoration. Also, the adhesive 12 attaching the tab to the restoration is transparent so that the light can pass through it as well.

Figure 4:
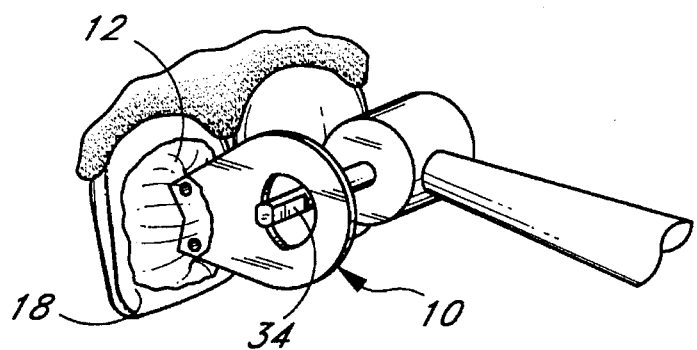
FIG. 4 is a view similar to FIG. 1 but with the tab gripped and positioned adjacent the tooth to which it is to be mounted.
Figure 5:
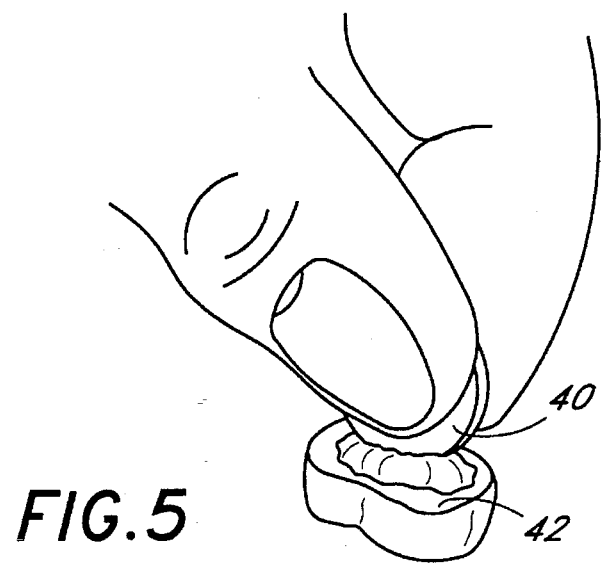
FIG. 5 is a perspective view illustrating an earlier form of a tab of the invention attached to the upper surface of a tooth crown.
Figure 6:
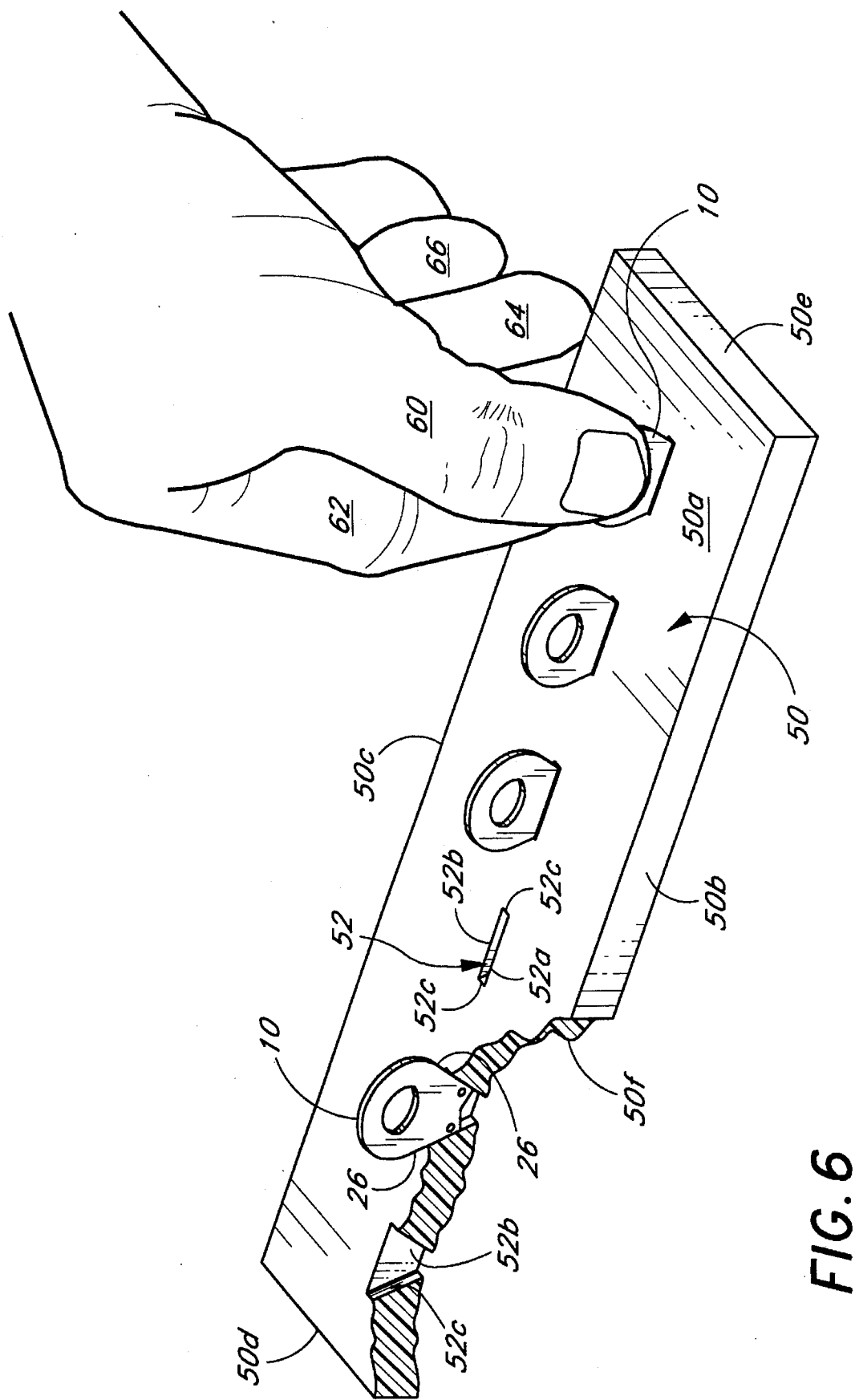
FIG. 6 is a perspective view illustrating a group of tabs positioned in a tab support.

The holder tab 10 may be used to position other restorations, such as dental crowns. Also, shapes other than that of the tab 10 may be utilized. Such use is schematically shown in FIG. 5, wherein the edge of a disc-shaped tab 40 is glued to the biting surface of a crown 42. The tab may be formed of glue, being sliced from a glue gun rod. In use, one curved edge is softened by heat, and pressed against the crown. The two point contact of FIG. 1 is preferable over the disc shape, but the disc is shown to illustrate that other generally thin flat shapes may be used. Of course the element 40 may be made of other materials, and glued to the crown in the manner described for the tab in connection with FIGS. 1 and 4.

To release a tab from a restoration, it is only necessary to spray the adhesive with water. This causes the adhesive characteristic to change enough so that it can be readily removed from the restoration. The restoration is at that stage securely bonded to the tooth so that the tab and the adhesive can be pulled away from the restoration without concern for any damage to the restoration or the tooth. The tab and the adhesive is then discarded.

Because the tabs 10 are such small elements, it is convenient to have them mounted in a vertical position with the finger gripping area extending upwardly so as to facilitate gripping between the thumb and forefinger of a dentist's hand. Further, it is desirable that a tab be gripped in a position to be attached to a restoration and positioned on a patient without regripping. FIG. 5 illustrates such an arrangement wherein a flat elongated rectangular or oblong, support 50 is shown having a row of slots 52 formed in its upper surface 50*a*. Each slot 52 is adapted to receive the lower end of one of the tabs 10. As seen, the support 50 has an elongated front wall 50*b* spaced from an elongated rear wall 50*c* and joined by short end or edge walls 50*d* and 50*e*. Further, each slot 52 has a generally rectangular cross-section with a front edge 52*a* and a rear edge 52*b* closely spaced from and parallel to the front and rear support walls 50*b* and 50*c*. The front and rear edges 52*a* and 52*b* of each slot are joined by short side edges 52*c*. As can be seen, the slots 52 are positioned and spaced in a side-edge-to-side-edge arrangement, with the slots being aligned in a row defined by the longer front and rear edges 52*a* and 52*b* of the slots.

The slots extend from the upper surface 50*a* of the support completely through the support, opening to a lower wall 50*f*. The upper end of each slot 52 is larger than the lower end. The slots are dimensioned so that when the lower end of a tab is positioned in a slot the side edges 26 on the lower end of the tab 10 engage the side edges 52*c* of the slot. The front to rear dimension of a slot is only slightly greater than the thickness of the tab, with the result that the tab is captured in the vertical position illustrated in FIG. 5. As seen, the front and rear surfaces of the tab are generally parallel to the front and rear walls of the support. The side edges 52*c* of the slots 52 taper gradually from the upper end to the lower end. Such taper is similar to the tapered edges 26 of the tabs 10. Thus the lower end of the tab nests in a slot 52 for easy insertion and removal from the slot. In a preferred form of the invention, the side edges 52*c* taper at an angle of about 22° and the upper end is about 0.3 inch in width between the side edges 52*c*. The upper ends of adjacent slots are spaced a little more than 0.2 inch.

The support 10 is desirably less than ½ inch thick, and preferably is only about a ¼ of an inch. Further, the front to rear dimension of the support is only about one inch, with the slots being centrally positioned between the front and rear walls. With this arrangement, the dentist or assistant may conveniently grip a tab 10 in its gripping area 30 with a thumb 60 and forefinger 62 while the middle finger 64 or ring finger 66 extends adjacent the rear wall of the support and downwardly onto the surface on which the support rests. This provides a stabilizing action for the operator's hand while gripping a small tab, as may be seen from FIG. 5.

It should be noted that the operator's fingers are gripping the tab from above which is the same position the operator's hand is typically oriented when the tab is attached to a veneer that is being positioned on a patient's front tooth. Thus, with the tab 10 so positioned, the operator can conveniently lift it from the support and hold it while the lower edge of the tab is dipped in glue and attached to a veneer. Typically the veneer is positioned on a dental cast adjacent the tab support. A finger from the operator's other hand is usually positioned behind the tooth on the dental cast on which the veneer has been positioned to support the veneer. The veneer may then be lifted by the tab and positioned on the patient's tooth or laboratory model, without the dentist having to release the tab until the veneer has been positioned on the patient's tooth. Thus the arrangement illustrated and described increases the efficiency of the operation and minimizes the risk of a veneer or a tab being dropped. By having a row of tabs supported in a row of slots, the operator can conveniently place a series of veneers on a patient's teeth or lab model.

While the tab system has been described in a manner primarily emphasizing the use of the tabs by the dentist in installing veneers, the tabs, as noted above, are also useful with other dental restorations. In addition to positioning restorations on the patient, the system is very useful in the laboratory where the restorations are being fabricated. Typically, the restorations must be handled a number of times in fabricating and inspecting them, and the tabs are convenient for holding the restorations during such operations.

What is claimed is:

1. A combination, comprising:
    a dental restoration having a surface to be bonded to a tooth and an outer surface which becomes a surface of the tooth when attached to the tooth;
    a generally thin, flat gripping element; and
    adhesive connecting an edge of said element to said restoration outer surface with said element extending generally perpendicular to said restoration outer surface so that the element forms a finger-gripping tab for facilitating placement of said restoration on a tooth or tooth model.

2. The combination of claim 1, wherein said element is sized to be conveniently gripped between the thumb and a finger of a person's hand, but the gripping areas on the thumb and finger are larger than the element.

3. The combination of claim 1, wherein said element is made of plastic and has a thickness of about 1 mm or less.

4. The combination of claim 1, wherein said element has a hole through it to facilitate gripping by a person's finger and thumb.

5. The combination of claim 1, wherein said element edge has a pair of spaced points which engage the restoration to provide two-point spaced contact with a curved restoration.

6. The combination of claim 5, wherein said edge includes a recess between said points, and said adhesive surrounds said edge of said element and extends into said recess to provide a firm connection to the restoration.

7. The combination of claim 1, wherein said adhesive is a thermoplastic material which softens when heated to facilitate flowing onto the restoration and the tab, but is solidified, although somewhat resilient, at room temperature.

8. The combination of claim 1, wherein said adhesive when solidified will release from said restoration when water is applied to it.

9. The combination of claim 1, including a vibrator engaging an edge of said element spaced from said adhesive to produce vibration in the plane of said element and into said dental restoration when the restoration is positioned on a tooth being restored, with bonding material between the restoration and the tooth.

10. The combination of claim 9, wherein said vibrator includes a shaft to be rotated with a side of the shaft engaging said element, said shaft having a cross section which vibrates the element when the shaft is rotated.

11. The combination of claim 10, wherein said element has a hole through it and said shaft extends through said hole and engages an edge of said hole.

12. The combination of claim 1, wherein said adhesive covers a major portion of said restoration outer surface.

13. A method of positioning a dental restoration on a tooth or tooth model, comprising:

attaching with an adhesive an edge of a generally thin, flat element to an exterior surface of the restoration, with the element extending generally perpendicular to said exterior surface of the restoration to form a finger-gripping tab; and gripping said tab between the thumb and finger of one hand close to the restoration so as to facilitate adjusting or positioning of the restoration on a tooth or tooth model.

14. The method of claim 13, wherein said attaching step includes applying a hot-melt adhesive to the restoration and said edge of said element.

15. The method of claim 13, wherein said attaching step includes applying a quantity of hot-melt adhesive directly to the exterior surface of said restoration, dipping said edge of said element into a quantity of hot-melt adhesive, and positioning the lower edge of said element and its adhesive onto the adhesive on said restoration.

16. The method of claim 13, including removing said adhesive and said element from said restoration by applying water to the adhesive.

17. The method of claim 13, including:

applying a permanent bonding material to said tooth and said restoration;

placing the restoration on said tooth; and positioning a vibrating tool against an edge of said tab to vibrate said restoration against said bonding material.

18. The method of claim 17, including positioning said vibrating tool through a hole in said tab and vibrating the tool against an edge of said hole toward said restoration.

19. The method of claim 18, wherein said positioning step includes positioning a small shaft through said hole with the side of said shaft engaging said edge said shaft being connected to be rotated by a dental handpiece, said shaft being designed to vibrate said tab when the shaft is rotated.

* * * * *